United States Patent [19]
John

[11] Patent Number: 5,611,350
[45] Date of Patent: Mar. 18, 1997

[54] METHOD AND APPARATUS FOR FACILITATING RECOVERY OF PATIENTS IN DEEP COMA

[76] Inventor: Michael S. John, 1010 Orienta Ave., Mamaroneck, N.Y. 10543

[21] Appl. No.: 598,376

[22] Filed: Feb. 8, 1996

[51] Int. Cl.⁶ ........................................ A61N 1/36
[52] U.S. Cl. ............................ 128/731; 128/732; 607/45
[58] Field of Search ................................. 128/731, 732, 128/733, 642; 607/2, 3, 45, 53, 54, 55, 56

[56] References Cited

U.S. PATENT DOCUMENTS

| Re. 34,015 | 8/1992 | Duffy | 128/731 |
| 3,892,227 | 7/1975 | Coursin et al. | 128/731 |
| 3,893,450 | 7/1975 | Ertl | 128/731 |
| 4,462,411 | 7/1984 | Rickards | 128/731 |
| 4,493,327 | 1/1985 | Bergelson et al. | 128/731 |
| 4,649,482 | 3/1987 | Raviv et al. | 128/731 |
| 4,702,254 | 10/1987 | Zabara . | |
| 5,269,303 | 12/1993 | Wernicke et al. | 607/45 |
| 5,331,969 | 7/1994 | Silberstein | 128/731 |
| 5,495,853 | 3/1996 | Yasushi | 128/732 |

*Primary Examiner*—Angela D. Sykes
*Assistant Examiner*—Stephen Huang
*Attorney, Agent, or Firm*—Eliot S. Gerber

[57] ABSTRACT

In a medical procedure to treat a patient in a deep coma, an electrode is implanted on the vagus nerve (tenth cranial nerve) in the patient's neck. A selected pulse train is generated and applied to the electrode as a treatment for the deep coma. The patient's brain waves are collected, amplified and digitized before, during and after the treatment, and compared, using a computer system, against a reference (the patient or/and a normal group) to determine if the treatment is helping the patient.

15 Claims, 1 Drawing Sheet

METHOD AND APPARATUS FOR FACILITATING RECOVERY OF PATIENTS IN DEEP COMA

FIELD OF THE INVENTION

The present invention relates to medicine and more particularly to electrical stimulation to revive patients from coma.

BACKGROUND OF THE INVENTION

At the present time there is considerable medical interest in reviving patients from coma. The term "coma" is used to describe a human patient's state of profound insensibility, i.e., the patient is unconscious and immobile. A "deep coma" is a coma lasting over one week.

Coma is distinguished from other mental impairments such as "dementia", which is a mental decrease in functioning, including lessened memory, in which the patient is conscious and generally mobile.

Coma as a medical symptom may be the result of many causes, including drug reactions and cardiovascular stroke. However, it is believed that the most common cause of coma is head injury, for example, head trauma in automobile accidents. A patient in coma may be emotionally and physically devastating to the patient's family. In addition, the care of coma patients is costly, for example, $300 to $1000 a day for hospital care, and imposes a burden on the health system. There are many cases of traumatic brain injury each year, with many leading to coma, including many who remain in a persistent vegetative state that may last from several days to more than a year.

Historically, recovery from coma has been demonstrated in laboratory animals. Adametz showed that when the recticular formation was removed in steps, giving the brain a chance to reorganize itself rather than all at one time, animals would not lose consciousness. Recent research has further explored the plasticity of the brain in humans, such as the work of Tsubowuawa and has shown successful treatment of the coma state by direct brain stimulation (electrodes implanted within the brain).

In U.S. Pat. No. 4,702,254 to Zabara an electric patch is applied, in a surgical operation, to the vagus nerve (tenth cranial nerve). The patient's brain waves may be sampled, by scalp EEG electrodes, and when the brain waves are abnormal they indicate the imminence of a convulsion (epileptic seizure). At that time a voltage pulse train is applied to the vagus electrode patch to prevent the convulsion.

In U.S. Pat. No. 5,269,303 to Wernicke an electrical stimulation signal is applied to an implanted electrode on the vagus nerve to treat dementia. The Wernicke patent mentions that the brain's thalamic and cortical areas are reached by vagal stimulation and states "vagal stimulation can be beneficial in treating dementia in its effect on the recticular formation or activating system, the network of neurons involved in controlling the level of alertness" (column 2, lines 35–38).

SUMMARY OF THE INVENTION

In accordance with the present invention, in a surgical procedure an electrical contact (electrode) is placed on the vagus nerve (the tenth cranial nerve), preferably in the neck of the patient who is in deep coma. The electrode has leads, through the skin, to an external connector. That operation may be simpler and safer than trying to implant electrodes in the brain.

After recovery from the electrode implant operation, an electrical stimulus is applied to the electrode through the connector from an external frequency generator. The frequency generator is controlled by a computer system which is programmed to provide a timed sequence of various pulse wave shapes, various frequencies and various voltage amplitudes ("program steps"). The patient's brain waves are detected and recorded using EEG electrodes removably attached to the patient's scalp.

The patient's brain waves are collected (i) prior to each step of the program, (ii) during application of the electrical stimulation, and (iii) subsequent to each step of the program.

The brain waves are digitized and artifact contaminated portions are rejected. The patient's brain waves prior to, and after, each program step are analyzed to determine if there is any improvement, or any change, due to the program step. If there has been an improvement, the program step (after verification of the improvement) is used in a course of treatment. In the event the patient stops improving, the program steps are repeated in the hope that a different program step may be effective.

DETAILED DESCRIPTION OF THE INVENTION

Introduction

Figure 1:
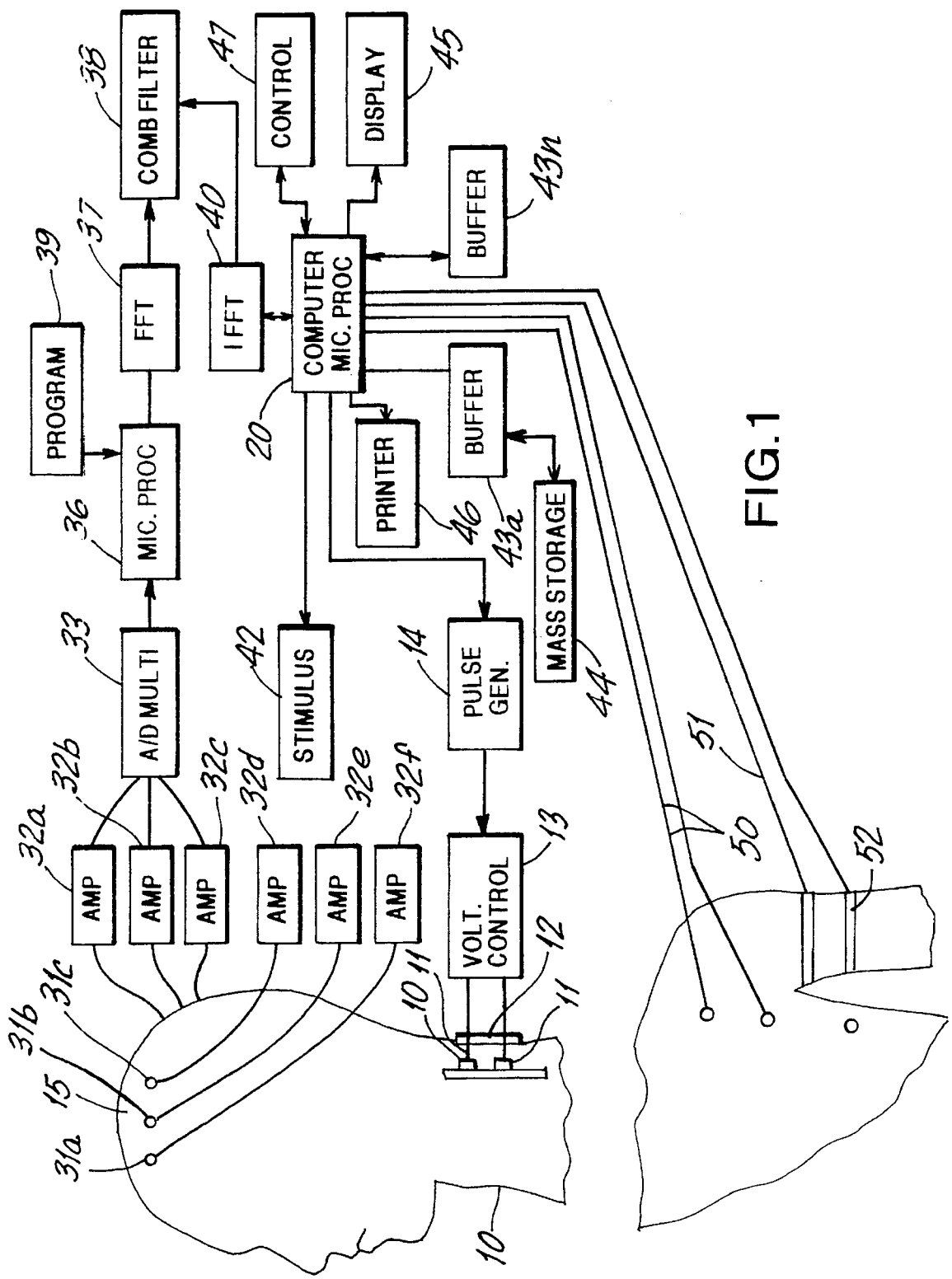
FIG. 1 is a block schematic drawing of the apparatus of the present invention.

The present invention is for a system and method of treating patients in deep coma (prolonged loss of consciousness or in a persistent vegetative state). For example, the patient's deep coma may be caused by traumatic head injury or a cerebrovascular accident.

As shown in FIG. 1, in a surgical procedure electrodes 10 are secured on the vagus nerve (tenth cranial serve) of the patient, preferably in the patient's neck 11. The electrodes 10 are connected to two encased conductors (lines) 11 which lead to an external connector plug 12. The plug is removably connected to a mating plug which is connected to a voltage control 13 and pulse generator 14. The pulse generator 14 produces a selected pulse train and the voltage control 13 provides a selected current amplitude or voltage to the waves of the pulse train, both under control from the computer system 20 (computer microprocessor).

The signal pulse generator 14 is capable of generating voltage wave trains of any form (sine, square wave, spike, rectangular, etc.) in a selectable voltage amplitude in the range of 0.1 volts to 5 volts and at a selectable frequency of 10 Hz to 500 Hz and with voltage amplitudes of 0.5 to 5 volts (at 75 Hz). The frequency generator is controlled by a digital computer system 20, for example, a PC (Personal Computer), such as an IBM "Activa" (TM) computer using Microsoft Windows 95 operating system and an Intel Pentium (TM) CPU (Central Processing Unit). The pulse trains of electrical waves to the implanted electrode constitutes an "electrical stimulation program". The device of the present invention includes a monitor of electrophysiological signals from the brain (EEG or EP), including preferably a set of electrodes removably adhered to the patient's scalp.

The device also preferably includes a monitor of the patient's autonomic nervous system measure (EKG, EMG, blood pressure) to ensure that the electrical stimulation program is not adversely affecting vital functions. If the program of stimulation begins to affect vital signs the stimulation is discontinued until an appropriately trained medical person evaluates the situation and decides on a new program of stimulation.

The device also contains a computer system to compare, and evaluate by statistical criteria, the patient's present brain state with a "reference state". The reference state may be a past state (a state of being defined as a set of values obtained from the patient, i.e., a self-norm) or a weighted past set of state, or derived from a database having a normative mean value of such signals for the patient's age. The normative mean value (based on a normal group) may take medical condition, and other relevant factors such as medications, into account. The EEG or EP data can be compared in the time or frequency domain, or a transform of these domains. The patient data can first be normalized as a standard score by means of the Z-transform.

An Electrode is Positioned on a Cranial Nerve

A "cranial nerve" is a peripheral nerve which has its central nervous system connection with the brain, as opposed to the spinal cord. Some of the cranial nerves can be reached by a surgical operation which is as close to the skin as may be suitable for an easily surgical implantable electrode (for example, the olfactory nerve first cranial nerve—fila olfactoria—special sensory nerve fibers to olfactory sensors). or vestibulocochlear cranial nerve (statoacoustic nerve—special sensory nerve fibers to the inner ear). In some patients, because of the locus of their head injury, it may be useful to use a cranial nerve which communicates with the injured portion. The cranial nerves enter the brain through a hole (foramen) in the skull.

Preferably sensory nerve fibers (carrying information from the periphery) are used for the electrode, rather than motor nerve fibers (carrying information from the brain to the periphery). The vagus nerve (tenth cranial nerve) is preferred as the location of the implanted electrode. The vagus nerve consists of both special visceral motor fibers, general visceral motor fibers, visceral sensor and special sensory fibers.

It is believed that electrical stimulation of a properly selected cranial sensory nerve, especially the vagus nerve, will be communicated to and activate the brain's reticular system. It is also believed that the reticular system is central in prolonging coma in many patients, but not all patients.

It is believed that the activation of the vagus nerve produces an effect on the recticular system via synaptic transmission. The recticular system is a relatively large and inhomogeneous structure extending from the hind-brain (medula) to the mid-brain (thalamus) with neural connections to the cerebral cortex and spinal cord. It is less practical to directly electrically activate the recticular system because of its large extent and proximity to vital centers.

Preferably two electrodes are wrapped about the vagus nerve in the patient's neck. A spiral anchoring tether for the electrodes is described in U.S. Pat. No. 4,979,511, incorporated by reference herein. That tether is an open helical design which is flexible and minimizes mechanical damage to the nerve.

It is known that the recticular system, (recticular formation system) is involved in alertness. The recticular system has reduced brain level activity during slow wave sleep. It is believed that electrical stimulation over time, of the recticular system, will reduce the length of coma in some patients.

Evaluation Mode

After the electrode is implanted on a cranial nerve, medical personnel can determine several stimulation parameters (pulse train sequences) which cause an improvement in the patient's condition as measured by the patient's EEG and EP brain waves. These stimulation parameters generally would include pulse amplitude, pulse shape, pulse width in rectangular shape, pulse frequency, pulse train duration and inter-train interval. These are selected from a screen display menu of suggested pulse sequences ("program steps") using the computer system. After a set of possibly advantageous stimulation parameters have been selected, they are programmed into the computer system 20. Those program steps that worsen the condition, as measured by the patient's brain waves or vital signs, are stored as a set of parameters that should be avoided.

Evaluation/Stimulator Mode

The stimulator can also function in an evaluation mode in which a series of other stimulation parameter combinations are automatically chosen and tested in a regular or random manner in an attempt to discover parameters which cause an improvement in the patient's condition. These "program steps" are part of an evaluation/stimulation program. Those program steps that produce an improvement, as measured by the patient's brain waves, are stored as a set of possible alternative parameters.

Treatment Mode

The device will begin to electrically stimulate a patient based upon some program of stimulation which has been determined by the above described tests. If the stimulation produces improvement of the patient's state of health, e.g., the clinical signs or monitored brain state indicates that the patient's brain state is moving closer toward that of a conscious state, the stimulation will proceed. If the stimulation fails to produce the desired state changes, after a specified interval, the stimulation parameters (program) will change. This process will continue until the comparison means indicate that a favorable type of stimulation has again been achieved. If a present program of stimulation begins to affect vital signs adversely, the stimulation is discontinued until an appropriately trained medical person evaluates the situation and decides on a new program of stimulation.

The device is preferably partially implantable (the electrode) and partially external (the EEG electrodes, the computer-comparison system and the stimulus pulse generator). However, alternatively the pulse train to the implanted electrodes may be generated by a surgically implanted pulse generator and implanted power source having a replaceable/rechargeable power supply.

Brain Wave Detection and Analysis

The patent is tested after the surgical operation and prior to treatment. A group of EEG electrodes (one or more electrodes) are removably secured to the scalp of the patient. Six EEG electrodes are preferably positioned as follows: front left ($F_3$), front right ($F_4$), center left ($C_3$), center right ($C_4$), back left ($P_3$) and back right ($P_4$), the capital letter F,C,P referring to position names in the International 10/20 Electrode Placement System. Two reference electrodes are linked and removably positioned on the mastoids, or other suitable location, to use as a reference for monopolar recording. A conventional EKG (electrocardiogram) electrode, on the patient's shoulder or chest, is used as ground.

The electrodes employ a standard electrolyte gel for contact and the impedances of each electrode-skin contact is below 5000 ohms. The EEG system, described below, checks the electrode-skin impedance at each electrode and displays a warning if any such impedance falls below 5000 ohms.

An EEG system operator collects a set of artifact-free EEG and EP samples. Alternatively, data acquisition may be computer controlled (automatic) with computer removal or exclusion of artifacts by regression or other techniques. The baseline session contains 60 seconds of EEG and EPs averaged using 2048 stimuli. The EEG system then subjects the data to spectral analysis using FFT (Fast Fourier Transform) and EP peak detection. Mean values and standard deviations are obtained for absolute ($uv^2$) and relative (%) power in the delta (1.5–3.5 Hz), theta (3.5–7.5 Hz), alpha (7.5–12.5 Hz) and beta (12.5–25 Hz) frequency bands.

As shown in FIG. 1, the patient's head 15 is connected with the desired number of electrodes 31a–31f (31d–31f not shown), preferably silver-silver chloride disk electrodes or less preferably needle electrodes. The drawing shows three electrodes.

The electrodes 31a–31f are connected to respective amplifiers 32a–32f, each electrode lead being connected to its own amplifier. Each amplifier 32a–32f has an input isolation switch, such as a photo-diode and LED coupler, to prevent current leakage to the patient. The amplifiers 32a–32f are high-gain low-noise amplifiers, preferably having a frequency range of 0.5 to 100 Hz, gain of 10,000 common mode rejection of 100 dB and noise of less than 1 microvolt peak-to-peak.

The amplifiers 32a–32f are connected to an analog-to-digital multiplexer 33 (A/D multiplexer). The multiplexer 33 samples the amplified analog brain waves at a rate compatible with the bandwidth of the amplifiers. The multiplexer 33 provides, at its output, sets of digital data, representing the EEG input analog signals. The multiplexer 33 is connected to the dedicated microprocessor 36. For example, the microprocessor may be an Intel Pentium (TM) or Intel 486. The dedicated microprocessor 36 is connected through its dedicated 512-point FFT 37 (Fast Fourier Transform) to digital comb filter 38 and is controlled by program 19.

The comb filter is connected to, and controls, the IFFT 40 (Inverse Fast Fourier Transform). The output of IFFT 40 is connected to the system microprocessor 20 (which may be Intel 486) which is connected to the stimulus devices 42 (lights, loudspeaker, shock device. etc.) to the system digital storage buffers 43a–43n (only two being shown), to the mass storage 44, such as a hard disk, to the display 45, such as a CRT, and a print-out printer 46 and to the control panel 47.

The digital comb filter 3.8 may be as described in U.S. Pat. No. 4,705,049, incorporated by reference herein. The comb filter may be considered a series of band pass and band stop filters arranged to be responsive over a selected range. The selected range is 0–1400 and there are band pass filters at 100–580 Hz, 600–640 Hz and 720–800 Hz and 900–1400 Hz and band-stop filters at 0–100 Hz, 580–600 Hz, 640–720 Hz, 800–900 Hz and above 1400 Hz. The band pass filters are the "teeth" of the comb and they are selected so as to accord with the frequencies in which the signal/noise ratio is acceptable. The band-stop filters are selected to be at frequencies in which the noise is excessive. The multiplexer is programmed by program 39, which may be obtained from a floppy disk, to obtain samples of the signal and of the noise. The noise is preferably obtained when there is an absence of evoked potential stimuli and the signal is obtained during epochs up to 600 milliseconds long, beginning with presentation of the stimuli or after a pre-selected delay.

The program and its controlled microprocessor condition the input signals and insure that they are valid biological signals. Such validity checks on the input signals include calibration measurement, impedance measurements and automatic artifact rejection algorithms.

The microprocessor 20 automatically provides a timed set of stimuli from stimulator 42 which may be an audio sound from a speaker, a visual signal from a light flash, or a tactile signal from an electric shock or a vibrator. Visual flashes may be delivered using LED goggles flashing at a rate of 1/second (VEP). Auditory clicks, about 100 dB 5PL, may be delivered through a stethoscope earpiece by air conduction tubes from a magnetic speaker. The rate of stimulus is preferably 7–50/second and most preferably 35–45/second, i.e., a 40 Hz auditory steady-state response (40 Hz-ASSR). Common clicks and rare flashes can be combined into a randomly mixed stimulus sequence, with the EP elicited by the rare stimulus providing the cognitive "event-related potential", P300 (P3). The patient's brain will respond to these stimuli providing "Evoked Potentials" (EP) which are averaged to reduce noise, providing an "Average Evoked Response" (AER). Sample size varies with stimulus mobility, ranging from 100 (VEP) to 512–2048 (BAER/BSER).

The AER is the sum of samples time-locked to the onset of the stimuli divided by the number of samples, to provide an updated average.

During the electrical pulse stimulation program, the patient is connected to the EEG system of FIG. 1.

The objective of the EEG monitoring during treatment is to provide the neurologist with additional clinical information regarding the state of the patient's brain.

In general, this involves the intermittent collection of periodic artifact-free on-going EEG sessions, and evoked potential challenges, for as long as the treatment lasts, the collection and analysis of data and comparisons of features extracted form that data to the self-norm (a past state of the patient).

The preferred list of measures (features) extracted by FFT before, during and after treatment, is as follows: For each of the six electrodes; 5 bands of absolute power (total, delta, theta, alpha, beta), for the three pairs of homologous electrodes; coherence of the total EEG and delta, theta, alpha, beta. This is a total of 84 univariate features for the on-going EEG. An overall multivariate measure of deviation, such as a mamalanobis distance, is compared for each lead and across the six leads, 7 more EEG features.

In addition to the collection and analysis of on-going EEG, discussed above, the patient is automatically subjected to suitable stimuli at selected intervals to provide sets of EPs (Evoked Potentials).

The principal measure of bilateral EP symmetry is the Pearson product-moment correlation (r) across the time bins, computed for EPs recorded from homologous derivations in left and right hemispheres ($C_3$ vs. $C_4$, $F_3$ vs. $F_4$ and $P_3$ vs. $P_4$, etc.) and referred to as "interhemispheric coherence". The square of the product-moment correlation coefficient ($r^2$) is also obtained for each homologous pair of derivations. The various features are then compared against the "baseline" (data collected from the pre-treatment) patient or a normal group or both. Each measure may be Z-transformed using the corresponding mean and standard deviation obtained from the baseline. Each Z-score for a patient is calculated in the following manner: the reference pre-treatment mean, X, for a particular measure, is subtracted from the value X for that measure obtained from the patient after the treatment to determine if a program step or treatment was beneficial. The difference, X–X, is divided by the standard deviation, s, of that measure for the baseline. Thus, $Z=(X-X)/s$. If the distribution of a variable is Gaussian, the Z-score provides an estimate of the probability that an observed measure is "abnormal", i.e., improbable.

In addition, the patient's measures are statistically compared with a normative reference database based on measures from a group of normal non-coma patients.

Alternatively, measures may be assessed by computing sensitive indices such as $$\frac{\text{delta plus theta}}{\text{alpha plus beta}} \quad \text{or} \quad \frac{\text{theta}}{\text{alpha}}$$

and calculating the ratio of such combined variables or of univariate values Another alternative to the Z-transform is to use the F-ratio derived form the variance within the samples divided by the variance of the baseline Statistically significant thresholds can be defined for each of these alternatives.

The system will combine measures, after having z-transformed them relative to the baseline, and display the combinations as "trajectories". Upper and lower alarm limits can be separately adjusted. The screen may show six trajectories (vectors) corresponding in location to the six EEG electrodes, plus one trajectory for every EP category.

Each patient is also connected to a set of EKG (electrocardiogram) electrodes 50 to detect changes in EKG waveshape and rate of heart activity and to EMG (electromyograph) electrodes 51 to detect muscle activity, to a blood pressure detector 52 (sphygmomanometer) to measure systolic, diastolic and pulse pressure, to sensors or respiration, expired $CO_2/O_2$ and body temperature. The EKG amplifier 53 and the EMF amplifier 54 and blood pressure device 55, respiration and temperature sensors, are connected to the computer system 20 and may be of conventional construction.

What is claimed is:

1. A method for treatment of deep coma of a patient, including the steps of:
   (a) surgically attaching an electrode to a cranial nerve of the patient, the electrode having electrical leads connected thereto;
   (b) generating a selected pulse train of electrical pulses and applying the pulse train through the electrical leads to the electrode;
   (c) deriving the patient's brain waves, after the application of the pulse train, using EEG electrodes removably secured to the patient's scalp;
   (d) amplifying and analyzing in a computer system, the derived brain waves by comparison against a reference;
   (e) based on the brain wave analysis, either continuing, discontinuing or changing the selected pulse train; and
   (f) stopping the application of the pulse train if the patient's vital signs decline into a dangerous range.

2. A method as in claim 1 herein the cranial nerve is the vagus nerve.

3. A method as in claim 1 and, after the application of the pulse train, stimulating senses of the patient to evoke the brain waves.

4. A method as in claim 1 and deriving the patient's brain waves, using EEG electrodes, prior to application of the pulse train, and using the pre-application derived brain waves as a reference in (d).

5. A method as in claim 4 wherein the reference in (d) includes brain waves derived from a normal group of patients.

6. A method as in claim 5 wherein the derived brain waves are on-going EEG brain waves, or evoked EP brain waves, or both EEG and EP.

7. A method as in claim 1 wherein the reference in (d) includes brain waves derived from normal group of patients.

8. A method as in claim 1 wherein the derived brain waves are on-going EEG brain waves, or evoked EP brain waves, or both EEG and EP.

9. A method as in claim 1 and deriving the patient's brain waves, using EEG electrodes, during the application of the pulse train and analyzing the so derived brain waves by comparison against a reference.

10. A method for treatment and monitoring of deep coma comprising:
    (a) surgically removably attaching an electrode to a cranial nerve of a patient;
    (b) removably connecting at least one EEG electrode to the patient's scalp;
    (c) presenting a set of stimuli to the patient and amplifying and digitizing brain wave evoked responses to the stimuli and the patient's ongoing brain wave activity collected from the EEG electrode to provide a first set of digital data representing the patient's brain waves in the patient's pre-treatment state and recording a first set of digital data in computer system memory;
    (d) generating a selected pulse train of electrical pulses and applying the pulse train to the electrode as a treatment of the patient's deep coma;
    (e) stopping the application of the pulse train of (d) if the patient's vital signs decline into a dangerous range;
    (f) after the treatment of (d), presenting another set of stimuli to the patient, which is the same as the set of stimuli presented in (c), and amplifying and digitizing the brain wave responses to the stimuli and the patient's on-going brain wave activity to provide a second set of digital data;
    (g) using a computer system and statistically comparing the first and second sets of digital data on a measure-by-measure basis; and
    (h) adjusting the pulse train applied to the electrode in a subsequent treatment in response to the comparison of (f) to help bring the patient out of the deep coma.

11. A method as in claim 10 and also statistically comparing the second set of data with a normative reference database based on a pre-selected group of normal persons.

12. The method of claim 11 and wherein statistically comparing the second set of data with the normative reference database also includes taking into account factors of weight, age and sex of the patient.

13. The method of claim 10 wherein stimuli for one or more modalities are presented, said modalities including (i) auditory modality and evoked responses are auditory responses (Audio Evoked Response), (ii) sensory modality and the evoked responses are brainstem somatosensory evoked responses (BSER), or (iii) visual modality.

14. The method of claim 10 wherein measures of ongoing EEG and the measures of the brainwave evoked response include at least one of the following measures for at least one user specified band: absolute power, relative power and coherence between a user specified set of electrodes.

15. The method of claim 10 wherein the measures of the brainwave evoked response include at least one of the following measures for user specified set of electrodes: signal strength, variability and interhemispheric symmetry.

* * * * *